United States Patent [19]

Cohen

[11] Patent Number: 5,121,979

[45] Date of Patent: Jun. 16, 1992

[54] DIFFRACTIVE MULTIFOCAL OPTICAL DEVICE

[76] Inventor: Allen L. Cohen, 10010 Walsham Ct., Richmond, Va. 23233

[21] Appl. No.: 456,226

[22] Filed: Dec. 22, 1989

Related U.S. Application Data

[63] Continuation of Ser. No. 280,899, Dec. 7, 1988, abandoned, which is a continuation-in-part of Ser. No. 863,069, May 14, 1986, Pat. No. 5,017,000.

[51] Int. Cl.⁵ .................. G02B 27/44; G02B 3/08; G02B 3/10; G02C 7/06
[52] U.S. Cl. .................................... 351/161; 351/168; 359/565; 359/569; 359/571; 359/742; 623/6
[58] Field of Search ............... 351/159, 161, 168–172, 351/162.2; 350/162.16, 162.22, 452, 437; 359/565, 569, 571, 742; 623/6

[56] References Cited

U.S. PATENT DOCUMENTS

| | | | |
|---|---|---|---|
| 3,004,470 | 10/1961 | Ruhle | 350/452 |
| 4,162,122 | 7/1979 | Cohen | 351/161 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,637,697 | 1/1987 | Freeman | 351/161 |
| 4,641,934 | 2/1987 | Freeman | 351/159 |
| 4,642,112 | 2/1987 | Freeman | 351/161 |

FOREIGN PATENT DOCUMENTS

| | | | |
|---|---|---|---|
| 63-85501 | 4/1988 | Japan | 350/452 |
| 602918 | 10/1958 | United Kingdom . | |
| 1154360 | 2/1967 | United Kingdom . | |

OTHER PUBLICATIONS

Genovese, F. C. et al., "Phase Plate Lens for a Multiple Image Lens System"; IBM Tech. Discl. Bulletin; vol. 8, No. 12; May 1966.
Ziegler, J. F., "Fabrication or Correction of Optical Lenses", IBM Technical Disclosure Bulletin, Mar. 1970.
Walsh, A., "Echelette Zone Plates for Use in Far Infrared Spectroscopy", Journel of the Optical Society of America, Mar. 1952.
Klein et al., "Multizone Bifocal Contact Lens Design", SPIE, Aug. 1986.
Tudorovskii, "An Objective With a Phase Plate", Optics & Spectroscopy, Feb. 1959.
Forst, Guntar, "Investigations into the Usability of Circular Gratings as Vision Aids", Augenoptiker, Dec. 12, 1966.
Myers, "Studies of Transmission Zone Plates", JOSA, vol. 19, 1951.
Miyamoto, "The Phase Fresnel Lens", Journel of the Optical Society of America, vol. 51, No. 1, Jan., 1961.
Waldman, "Variations of the Fresnel Zone Plate", Journel of the Optical Society of America, vol. 56, No. 2, Feb., 1966.
Horman et al., "Zone Plate Theory Based on Holography", Applied Optics, vol. 6, No. 2, Feb. 1967.
Stigliani et al., "Resolving Power of a Zone Plate", Journel of the Optical Society of America, vol. 57, No. 5, May, 1967.
Chau, H. H. M., "Zone Plates Produced Optically", Applied Optics, vol. 8, No. 6, Jun. 1969.
Jordan et al., "Kinoform Lenses", Applied Optics, vol. 9, No. 8, Aug., 1970.
Bottema, M., "Fresnel Zone-Plate Diffraction Patterns", Journal of the Optical Society of America, vol. 59, No. 12, Dec. 1969.
Young, M., "Zone-Plates and Their Aberrations", Journal of the Optical Society of America, vol. 62, No. 3, Aug., 1972.

(List continued on next page.)

Primary Examiner—Scott J. Sugerman
Attorney, Agent, or Firm—Finnegan, Henderson, Farabow, Garrett & Dunner

[57] ABSTRACT

A bifocal lens of the Cohen lens design utilizing phase zone plate optics and a facet depth of one-half wavelength of the design wavelength, where the primary focal points are at two ordes, specifically the $0^{th}$ and $1^{st}$ orders, and the brightness at each primary focal point is equal at about 0.40.

19 Claims, 1 Drawing Sheet

OTHER PUBLICATIONS

Kleinhans, W. A., "Aberrations of Curved Zone Plates and Fresnel Lenses", Applied Optics, vol. 16, No. 8, Jun., 1972.

Gomez-Reino et al., "Placas Zonales de Amplitud y Fase: Teoria y Realizacion Experimental", Optica Pura y Aplicada, vol. 10, 1977.

Vereshchagin et al., "Chromatic Properties of Profiled Zone Plates; Continuation", Opt. Spectrosc. (USSR) 47(1), Jul. 1979.

Kyuragi et al., "Higher-Order Suppressed Phase Zone Plates", Applied Optics, vol. 24, No. 8, Apr. 15, 1985.

Fincham et al., "Optics", Butterworths, London, 9th ed., 1980, pp. 72-75.

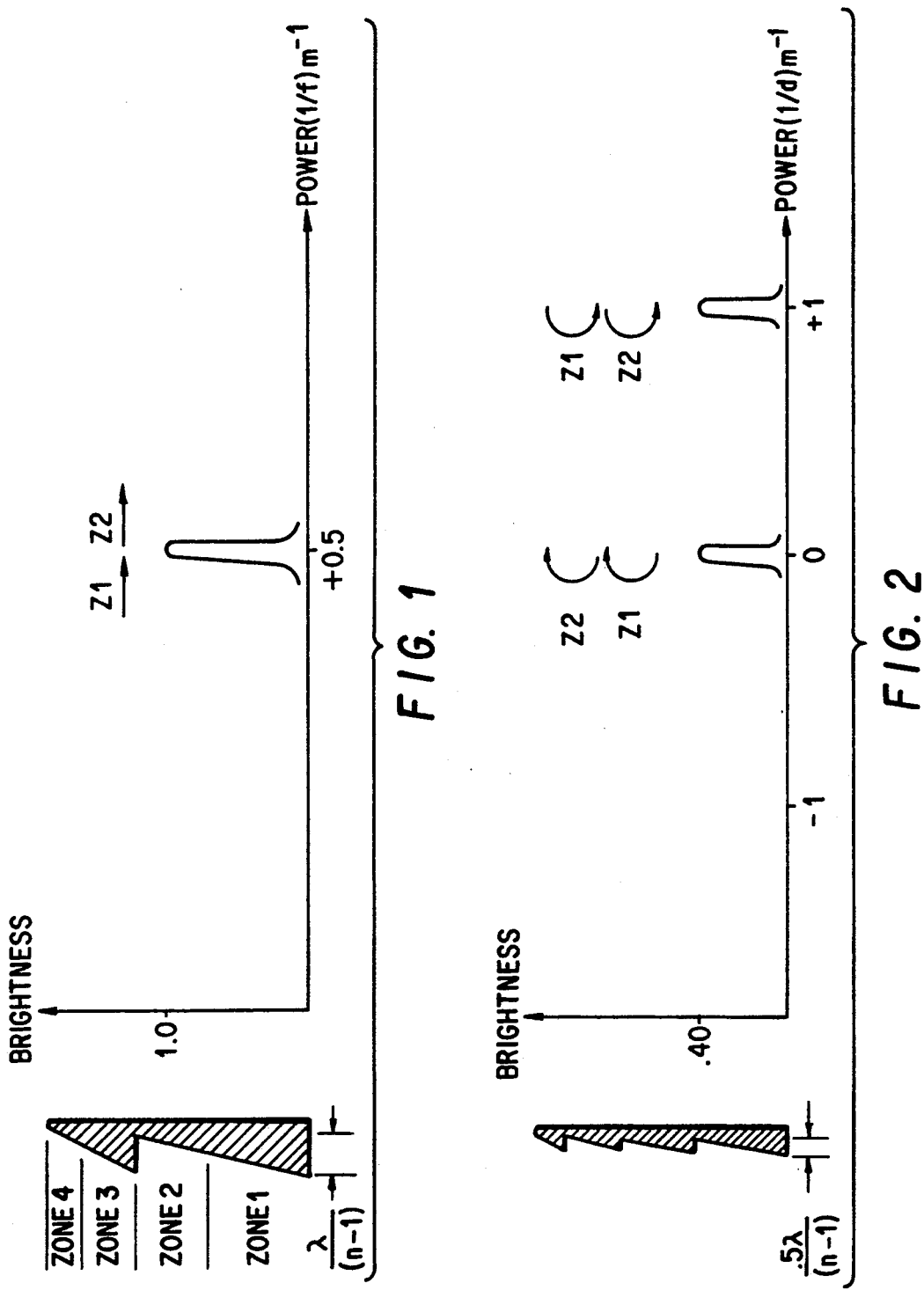

DIFFRACTIVE MULTIFOCAL OPTICAL DEVICE

RELATED APPLICATIONS

This application is a continuation of application Ser. No. 07/280,899 filed Dec. 7, 1988 now abandoned, which is a continuation-in-part of commonly owned U.S. application Ser. No. 863,069, filed May 14, 1986, now U.S. Pat. No. 5,017,000; and is related to the following commonly owned U.S. patent applications: Ser. No. 120,265, filed Nov. 12, 1987, now U.S. Pat. No. 4,881,804; Ser. No. 120,262, filed Nov. 12, 1987, now U.S. Pat. No. 4,881,805; Ser. No. 222,000, filed Jul. 20, 1988; and Ser. No. 237,292, filed Aug. 22, 1988, now abandoned.

BRIEF DESCRIPTION OF THE INVENTION

An improvement in multiple focal point profiled phase plate having blazed facets comprising a plurality of annular concentric zones spaced according to the formula $$r_k = \sqrt{\text{constant} \times k}\ ,$$

where k is a zone and is equal to 1, 2, 3, etc.; $r_k$ is the zone radii; the improvement comprising the incorporation of a repetitive step in the profile which has an optical path length (or depth) equal to one-half wavelength whereby to provide two focal points of equal brightness at about 0.40 of the incident light transmitted through the phase plate.

BACKGROUND TO THE INVENTION

This invention relates to an improvement in phase zone plate optics that embraces contact and intraocular lenses. A "phase zone plate", as employed herein and in the claims, is a unitary optical region of a lens utilizing the combination of a zone plate and optical facets (such as in the form of echelettes) in the zones of the zone plate, and the combined facets in the zones diffract light to produce a specific wavefront which results in a specific intensity distribution of light at a variety of orders (e.g., $0^{th}$, $1^{st}$, etc.) of the zone plate. The orders constitute the foci of the zone plate. In a restrictive sense and also in the most utilitarian sense, the phase zone plate is designed for general lens applications where the distribution of light at effective intensities is dependent upon zone spacing for yellow light. Yellow light, as employed herein, is that portion of the visible spectrum at 530–570 nanometers.

This invention relates inter alias to contact lenses. Contact lenses are classical vergency type lenses. They possess a concave corneal bowl (the posterior surface) that allows fitting to the eye and the outer surface (the anterior surface) is smooth and shaped to allow the eyelid to slide over the eye and to provide proper verging of light (taking the lens material's refractive index into consideration) to a focal point accommodating to the eye. The majority of the commercial contact lenses are shaped such that the lenses are thinnest about the optical axis and the thickness of the lenses gradually increases along a sloped radial length extending from the optical axis toward the lens perimeter. Owing to this variation in thickness, light passing through the optical axis has to pass through less lens material. Because light travels faster in air than it does through the lens, the light passing through the thicker portions of the lens will be shifted, hence be retarded in time. [1] Consequently, the shape of the lens is selected to accommodate this progressive retardation of the light so that the lightwaves emanating from the posterior surface are in synchronization in reaching a desired focal point.

[1]. See Fincham, et al., *Optics*, Published by Butterworths, London, 9$^{th}$ edition, 1980, 1981, pages 72–75.

This invention concerns contact lenses utilizing phase zone plate optics such as phase zone plate bifocals and "tuned" Fresnel lenses making use of concentric annular zones. Such lenses generally follow the designs described, for example, by Allen L. Cohen in U.S. Pat. Nos. 4,210,391; 4,338,005; and 4,340,283 ("Cohen patents"). A Cohen lens design provides that the radii "$r_k$" of the annular and concentric zones are substantially proportional to $\sqrt{k}$ and that the zones are cut so as to direct light to more than one focal point.

The Cohen lens design with phase zone plate optics allows bifocal lens constructions which are exceptionally thin. Contact lenses may be designed with phase zone plate optics in order to achieve a bifocal or other multifocal effects. The specific chromatic properties of a phase zone plate may be incorporated in the design of a contact lens including a contact lens having multifocal properties. All phase zone plate optical elements which are designated bifocals are possessed inherently with the ability to focus light to more than two focal points. They are designated bifocals because the intensity levels of the light to any two orders, e.g., the $0^{th}$ and $1^{st}$ order focal points are adequate for bifocal applications. In that sense, every bifocal distributes light to a third, and possibly more, focus. The judgement of whether a lens is a bifocal or trifocal is not based on any strict rule. If the wearer of the lens does not find objectionable the presence of the third or more focuses, then the lens is probably adequate as a bifocal. [2]

[2]. See Klein and Ho, *SPIE*, August 1986, Table 2 and the comments about Table 2.

Other references mentioning or suggesting phase zone plate optics in regards to contact lenses are G. Forst, "Research into the Usability of Circular Grids as Aid to Vision," *Der Augenoptiker*, 1966 (12), pages 9–19; Ziegler, "Fabrication or Correction of Optical Lenses," as modified by Cohen, see column 4, lines 27–36 of Cohen, U.S. Pat. No. 4,339,005, and column 5, line 63 to column 6, line 68, of Cohen, U.S. Pat. No. 4,210,391; Freeman, U.S. Pat. No. 4,637,697; and Freeman, U.S. Pat. No. 4,642,112 (to the extent that holography embraces phase zone plate optics).

A full-period zone, for purposes of this invention, is defined as the smallest repetitive sequence of facets within a phase zone plate which are spaced substantially proportional to $\sqrt{k}$. Such spacing is characterized by the formula:

$$r_k = \sqrt{2kf\lambda}$$

where f represents the $1^{st}$ order focal length. A half-period zone, for the purposes of this invention, is characterized by the formula:

$$r_k = \sqrt{kf\lambda}$$

where f represents the $1^{st}$ order focal length.

The non-refractive step wall or riser to the plateau of the step is cylindrical or nearly cylindrical in the planar direction of the optical axis of the lens, and thereby occupies a small fraction of the lens phase zone plate surface area.

SUMMARY OF THE INVENTION

This invention relates to a bifocal lens of the Cohen lens design utilizing phase zone plate optics and a facet depth of one-half wavelength of the design wavelength, where the primary focal points are at two orders, specifically the $0^{th}$ and $1^{st}$ orders, and the brightness at each primary focal point is equal at about 0.40.

This invention relates to an improvement in multiple focal point profiled phase plate having blazed facets comprising a plurality of annular concentric zones spaced according to the formula $$r_k = \sqrt{\text{constant} \times k},$$

where k is a zone and is equal to 1, 2, 3, etc.; $r_k$ is the zone radii; the improvement comprising the incorporation of a repetitive step in the profile which has an optical path length (or depth) equal to one-half wavelength whereby to provide two focal points of equal brightness at about 0.40 of the incident light transmitted through the phase plate.

The diffractive bifocal optical element of the invention comprises a phase zone plate containing annular concentric zones in which the zones are spaced substantially proportional to $\sqrt{k}$, the zones possess stepped blazed facets with a depth having an optical path length equal to $\lambda/2$.

The invention also embraces a phase zone plate containing annular concentric zones possessing facets which provide an alternating stepped repetitive pattern in accordance with $\sqrt{k}$ spacing in the optical element and wherein the depth of the steps of the facets are equal to $\lambda/2(\eta'-\eta)$, where $\eta'$ and $\eta$ are the indices of refraction of the lens and the medium in which the lens is interacting and $\lambda$ is the design wavelength. Importantly, the bifocal lens of the invention splits the transmitted incident light to two focal points in essentially equal intensities at about 0.40.

In another aspect, the invention encompasses a bifocal optical element of the Cohen design comprising a faceted step phase zone plate containing an alternating profile wherein:

a. the phase zone plate conforms to $r_k \approx \sqrt{2 k f \lambda}$;
b. the alternating profile occurs within the full-period spacing;
c. the facets have a depth of about $\lambda/2$; and
d. the zones are cut so as to direct yellow light to at least two primary focal points in equal intensity at about 40% of the transmitted light.

This invention relates to an ophthalmic lens such as contact and intraocular lenses containing such optical elements in which the ophthalmic lens is a bifocal lens that splits the light to two focal points in essentially equal intensities.

The invention employs an optical device as a contact lens, a spectacle lens, an intraocular lens implant, or a mirror.

The invention relates to a multiple focal point profiled phase plate, wherein a repetitive step is incorporated into the profile, whereby to cause a constant shift in the optical path length across essentially the entire zone into which it is incorporated. The phase plate is designed to operate as a multifocal lens in the visible light range. Such embodiments of the invention design the body means of said phase plate as a contact lens or as a camera lens.

BRIEF DESCRIPTION OF THE DRAWINGS

FIG. 1 shows a portion of the profile of a blazed lens with a single focal power, and its corresponding graph of brightness vs. focal power, showing the single focal point.

FIG. 2 shows a portion of the profile of the lens of FIG. 1 wherein a repetitive step is incorporated into the profile, and its corresponding graph of brightness vs. focal power, showing two focal points of equal brightness at about 0.4.

DETAILS OF THE INVENTION

The invention relates to a diffraction bifocal optical element. It utilizes a circularly blazed diffraction grating as encompassed by the Cohen lens design to achieve its multifocal properties. The blazed grating allows for adjusting the split of light between two focal points by adjusting the facet depth and providing the traditional parabolic profile in the blazed facet.

The invention includes a diffractive bifocal optical element comprising a phase zone plate containing annular concentric zones in which the zones are spaced substantially proportional to $\sqrt{k}$, the zones possessing blazed facets with a depth (or optical path length) equal to $\lambda/2$. The invention also embraces a phase zone plate containing annular concentric zones possessing facets which provide an alternating stepped repetitive pattern in accordance with $\sqrt{k}$ spacing in the optical element and wherein the depth of the steps of the facets are equal to $\lambda/2(\eta'-\eta)$, where $\eta'$ and $\eta$ are the indices of refraction of the lens and the medium in which the lens is interacting and $\lambda$ is the design wavelength. Importantly, the bifocal lens splits the transmitted light to two focal points in essentially equal intensities at about 0.40.

This invention concerns inter alia bifocal optical lenses comprising an optic zone section which uses diffractive means for achieving multifocal properties. The diffractive means incorporates a repetive pattern with a select facet depth of $\lambda/2$ whereby to provide what appears to be the optimum split of the transmitted light to two focal points, particularly at the $0^{th}$ and the $1^{st}$ orders.

The invention embraces a diffraction bifocal optical element superimposed on, etched into and/or embedded within a surface layer of a lens possesssing the ability to independently converge light in equal intensity to two primary focal points. A desirable aspect of the invention is the excellent intensity of light at the designed focal points. Subsequent to this invention, Klein and Ho, supra, confirmed the unique optimum split of the transmitted light to two focal points, particularly at the $0^{th}$ and the $1^{st}$ orders. According to Klein and Ho, the following intensities at the orders (m) are achieved for the bifocal lens of this invention:

| m = | 3. nonalternating (b = .5) |
|---|---|
| −4 | .0050 |
| −3 | .0083 |
| −2 | .0162 |
| −1 | .0450 |
| 0 | .4053 |
| 1 | .4053 |
| 2 | .0450 |

| m = | 3. nonalternating (b = .5) |
|---|---|
| 3 | .0162 |
| 4 | .0083 |

In a multifocal lens, the incident light is shared between the various primary focal points. It is an important objective that the various image brightness at each of the primary focal points be substantially equal in intensity otherwise shifting from one focal point to another will become disconcerting because the less intense image is affected adversely the more intense image. As a consequence of the difference in intensity of the images, the lesser image becomes weakened by the stronger image and bifocality becomes washed out because the lesser image is difficult to focus on. The present invention makes use of the fact that in multifocals that utilize diffraction lens designs, where the radii of the zones substantially obey the formula that is given by $r_k = \sqrt{\text{constant} \times k}$ and the zones are defined by facets depth of $\lambda/2$, the lens is a bifocal wherein the two primary focal points are at the $0^{th}$ and $1^{st}$ orders and the brightness at each of the two primary focal points comprises 40% of the transmitted incident light.

FIG. 1 describes a monofocal phase plate which is a +0.5 Diopter monofocal configured in the usual way by cutting blazed facets one-wavelength deep, where a blazed facet is taken to be an angled cut as opposed to a flat step cut. The facets in FIG. 1 are marked off in half-period zones. A full-period zone, defined as the smallest repetitive sequence of facets, comprises two half-period zones, i.e., zones 1 and 2, zones 3 and 4, and the like. The radii $r_k$ of the half-period zones for this monofocal phase plate is determined by the formula:

$$r_k \simeq \sqrt{kf\lambda}$$

where f represents the $1^{st}$ order focal length for this monofocal lens.

A uniform step with an optical path length (or depth) equal to one-half wavelength, may be incorporated into every odd zone of the profile as indicated by the dotted line of FIG. 1. The resulting lens is a bifocal phase plate and is shown in FIG. 2. The smallest repetitive sequence of facets inherent in that bifocal is such that the half-period zones of the monofocal lens have become the full-period zones of the bifocal lens. The radii $r_k$ of the half-period zones for the bifocal lens is determined by the formula:

$$r_k \simeq \sqrt{0.5kf\lambda} \quad f = 2.0 \text{ meter}, \quad (1^{st}\text{ order focus of monofocal})$$

or $$r_k \simeq \sqrt{kd\lambda} \quad d = 1.0 \text{ meter}. \quad (1^{st}\text{ order focus of bifocal})$$

where d represents the $1^{st}$ order focal length for the bifocal lens.

While the monofocal phase plate has a single focal power at first order, the bifocal phase plate exhibits two focal powers, one at the first order and in addition, one at the zeroth order. The first order focal point of the monofocal lens of FIG. 1 has a focal power equal to 0.5 Diopters (i.e., 1/f). But the first order focal point of the bifocal lens of FIG. 2 has a focal power equal to 1.0 Diopters (i.e., 1/d). The zeroth order focal power of the bifocal is 0.0 Diopters.

A unique and unexpected result of incorporating a uniform step with an optical path length (or depth) equal to one-half wavelength into every odd zone of the monofocal profile is a bifocal utilizing zeroth and plus first order focal points. Previously, the Wood Zone Plate (R. W. Wood, *Physical Optics*, Macmillan Co., New York, NY, 1914, pages 37–40, 217 and 218) was the only bifocal phase plate that split incident light to two focal points in essentially equal intensities at about 0.40. However, the Wood Zone Plate utilized minus first and plus first order focal points. But minus first order focal points have unwanted chromatic aberrations while zeroth order focal points do not have these aberrations. Hence, replacing the minus first order focal point with a zeroth order focal point, as this bifocal configuration does, represents an improvement in bifocal technology.

I claim:

1. A diffractive bifocal ophthalmic ocular lens in which the improvement comprises a phase zone plate optic including a plurality of blazed facets, each of the facets being blazed with the same angle and having a depth corresponding to an optical path length of one-half wavelength of a design wavelength within the visible spectrum so that light incident on the lens converges to primary focal points at adjacent diffraction orders, and so that the brightness at the design wavelength at the primary focal points is essentially equal to about 0.40 of the brightness of the incident light at the design wavelength.

2. A lens as recited in claim 1 wherein the design wavelength is between 530 nanometers and 570 nanometers.

3. A lens as recited in claim 1, wherein the blazed facets are disposed so that the adjacent orders correspond to the $0^{th}$ and $1^{st}$ orders.

4. A diffractive bifocal ophthalmic ocular lens comprising a profiled phase plate having a plurality of equally blazed annular concentric zones spaced according to the formula $$r_k = \sqrt{\text{constant} \times k} ,$$

where k=1, 2, 3, ... ; k is a zone; and $r_k$ is a zone radii; in which a repetitive blazed step with an optical path length equal to one-half wavelength of a design wavelength within the visible spectrum is incorporated in the profile so that light incident on the lens converges to two focal points at adjacent diffraction orders with essentially equal brightness of at least 0.40 of the incident light at the design wavelength at the focal points.

5. A diffractive bifocal ophthalmic ocular lens comprising a phase zone plate including annular concentric zones, each of the zones having a zone number, in which the zones are spaced substantially proportional to the square root of the zone number, and the zones possess equally blazed facets that have a depth with an optical path length equal to half of a wavelength of a design wavelength within the visible spectrum, so that the lens causes light of the design wavelength incident on the lens to converge to two focal points corresponding to adjacent diffraction orders in essentially equal intensities of at least 0.40 of the incident light at the design wavelength.

6. A diffractive bifocal ophthalmic ocular lens comprising a phase zone plate including annular concentric zones possessing blazed facets having equal blaze angles, the blazed facets providing an alternating stepped repetitive pattern in the lens, the depth of the steps of the facets are equal to $\lambda/2(\eta'-\eta)$, where $\eta'$ and $\eta$ are the indices of refraction of the lens and a medium in which the lens interacts and $\lambda$ is a design wavelength within the visible spectrum, so that the phase zone plate causes light of the design wavelength incident upon the lens to converge to two focal points corresponding to adjacent diffraction orders in essentially equal intensities at about 0.40 of the incident light of the design wavelength.

7. A diffractive bifocal ophthalmic ocular lens comprising an optical region zone disposed about an optical axis and a profiled phase zone plate disposed in the optical region for causing light of a design wavelength and incident upon the lens to converge to two adjacent focal points corresponding to adjacent diffraction orders, the phase zone plate comprising a plurality of blazed facets having equal blaze angles and a plurality of annular concentric zones spaced proportional to the square root of n, where n is an integer zone number measured along the lens radially outward from the optical axis to a periphery of the phase zone plate, the facets having a depth equal to approximately one-half the design wavelength.

8. A lens as recited in claim 7 wherein the blazed facets are disposed so that the brightness of the light at each of the focal points is about 0.40 of the light incident on the lens.

9. A lens as recited in claim 7 wherein said adjacent diffraction orders are the 0th and 1st orders.

10. A diffractive ophthalmic ocular lens with two primary focal points located at adjacent diffraction orders, the lens comprising a lens material and including a plurality of equally blazed annular concentric zones with selected zones separated by steps having step heights, the step heights being substantially equal to $\lambda/2(\eta'-\eta)$, where $\eta'$ and $\eta$ are the indices of refraction of the lens material and an adjacent medium, respectively, and $\lambda$ is a design wavelength within the visible spectrum, to cause light at the design wavelength and incident upon the lens to be focussed to each of the two primary focal points in essentially equal intensities, the intensities being substantially 0.40 of the incident light at the design wavelength.

11. A lens as recited in claim 10 wherein the lens is in the form of a contact lens or intraocular lens; and
  wherein at least one of the two focal points corresponds to the zeroth diffraction order.

12. A lens as recited in claim 11 wherein the design wavelength is between 530 nanometers and 570 nanometers.

13. A lens as recited in claim 10 wherein the lens is in the form of a contact lens or intraocular lens; and
  wherein the two focal points correspond to the zeroth and plus first diffraction orders, respectively.

14. A lens as recited in claim 13 wherein the design wavelength is between 530 nanometers and 570 nanometers.

15. A diffractive bifocal ophthalmic lens comprising annular concentric zones wherein the zones are blazed with the same angle and with a depth having an optical path length substantially equal to one-half of a design wavelength within the visible spectrum to cause the intensity of light at a design wavelength and incident upon the lens to be focused to two bifocal powers so that the intensity of the light at each bifocal power is at least 0.40 of the intensity of the light incident upon the lens.

16. A lens as recited in claim 15 wherein the lens is in the form of a contact lens or intraocular lens; and
  wherein at least one of the two focal points corresponds to the zeroth diffraction order.

17. A lens as recited in claim 16 wherein the design wavelength is between 530 nanometers and 570 nanometers.

18. A lens as recited in claim 15 wherein the lens is in the form of a contact lens or intraocular lens; and
  wherein the two focal points correspond to the zeroth and plus first diffraction orders, respectively.

19. A lens as recited in claim 18 wherein the design wavelength is between 530 nanometers and 570 nanometers.

* * * * *